US008885166B2

(12) United States Patent
Bianchessi et al.

(10) Patent No.: US 8,885,166 B2
(45) Date of Patent: Nov. 11, 2014

(54) ANALYZER FOR BIOCHEMICAL ANALYSES AND METHOD OF DETERMINING CONCENTRATIONS OF FLUORESCENT SUBSTANCES IN A SOLUTION

(75) Inventors: Marco Angelo Bianchessi, Melzo (IT); Maria Eloisa Castagna, Catania (IT); Federica Guerinoni, Agrate Brianza (IT); Alessandro Cocci, Agrate Brianza (IT)

(73) Assignee: STMicroelectronics S.R.L. (IT)

( * ) Notice: Subject to any disclaimer, the term of this patent is extended or adjusted under 35 U.S.C. 154(b) by 251 days.

(21) Appl. No.: 13/338,777

(22) Filed: Dec. 28, 2011

(65) Prior Publication Data

US 2013/0004954 A1    Jan. 3, 2013

(30) Foreign Application Priority Data

Dec. 30, 2010   (IT) .............................. TO2010A1089

(51) Int. Cl.
*G01N 21/25* (2006.01)
*G01N 21/64* (2006.01)

(52) U.S. Cl.
CPC .... *G01N 21/6452* (2013.01); *G01N 2201/0221* (2013.01); *G01N 2021/6441* (2013.01); *G01N 2021/6421* (2013.01); *G01N 21/6428* (2013.01); *G01N 2021/6419* (2013.01)
USPC .......................................... 356/417; 356/406

(58) Field of Classification Search
CPC .............. G01N 2021/6419; G01N 2021/6421; G01N 2021/6441; G01N 21/6428; G01N 21/6452; G01N 2201/0221
USPC ..................... 356/417, 317–318, 72–73, 406; 250/458.1–461.2; 422/82.07–82.08; 348/222.1–238
See application file for complete search history.

(56) References Cited

U.S. PATENT DOCUMENTS

| 3,619,061 | A | * | 11/1971 | Mitchell ....................... 356/317 |
| 3,715,163 | A | * | 2/1973 | Mitchell ....................... 356/317 |
| 5,817,462 | A | * | 10/1998 | Garini et al. ....................... 506/9 |
| 5,880,473 | A | * | 3/1999 | Ginestet ..................... 250/458.1 |
| 6,036,920 | A | * | 3/2000 | Pantoliano et al. ............. 422/67 |
| 6,071,748 | A | * | 6/2000 | Modlin et al. ................ 436/174 |
| 6,144,448 | A | * | 11/2000 | Mitoma ........................ 356/317 |
| 6,198,107 | B1 | * | 3/2001 | Seville ........................ 250/458.1 |
| 6,798,509 | B2 | * | 9/2004 | Sonehara et al. ............. 356/344 |

(Continued)

FOREIGN PATENT DOCUMENTS

| IT | TO20101089 | 12/2010 |
| WO | WO2007/119067 | 10/2007 |
| WO | WO2010/088514 | 8/2010 |

*Primary Examiner* — Michael A Lyons
*Assistant Examiner* — Shawn Decenzo
(74) *Attorney, Agent, or Firm* — Boulware & Valoir (57) ABSTRACT

An analyzer for biochemical analysis includes a seat for receiving a recipient. A first light source and a second light source illuminate the recipient with a luminous radiation, respectively, in a first excitation band and in a second excitation band, including a first excitation wavelength and a second excitation wavelength of fluorophores of a first type and of a second type. A first image sensor and a second image sensor are oriented so as to receive light emitted by fluorophores contained in the recipient and are, respectively, provided with a first detection filter and a second detection filter, having, respectively, a first detection passband and a second detection passband, including, respectively, a first emission wavelength and a second emission wavelength of the fluorophores of the first type and of the second type.

7 Claims, 7 Drawing Sheets

(56) References Cited

U.S. PATENT DOCUMENTS

| | | | |
|---|---|---|---|
| 6,914,250 B2 * | 7/2005 | Seville | 250/458.1 |
| 7,289,217 B2 * | 10/2007 | Boege et al. | 356/417 |
| 7,295,316 B2 * | 11/2007 | Boege et al. | 356/417 |
| 7,315,376 B2 * | 1/2008 | Bickmore et al. | 356/417 |
| 7,928,408 B2 * | 4/2011 | Ok et al. | 250/458.1 |
| 8,137,616 B2 * | 3/2012 | Sagner et al. | 422/50 |
| 2003/0139886 A1 * | 7/2003 | Bodzin et al. | 702/28 |
| 2006/0073483 A1 * | 4/2006 | White et al. | 435/6 |
| 2006/0129327 A1 * | 6/2006 | Kim et al. | 702/19 |
| 2007/0291257 A1 * | 12/2007 | Benjamin Tsai et al. | 356/73 |

* cited by examiner

ANALYZER FOR BIOCHEMICAL ANALYSES AND METHOD OF DETERMINING CONCENTRATIONS OF FLUORESCENT SUBSTANCES IN A SOLUTION

BACKGROUND

1. Technical Field

The present disclosure relates to an analyzer for biochemical analyses and to a method for determining concentrations of fluorescent substances in a solution.

2. Description of the Related Art

As is known, the analysis of nucleic acids includes, according to different modalities, preliminary steps of preparation of a specimen of biological material, amplification of the nucleic material contained therein, and hybridization of individual target or reference strands, corresponding to the sequences sought. Hybridization takes place (and the test yields a positive outcome) if the specimen contains strands complementary to the target strands.

At the end of the preparatory steps, the specimen is examined for checking whether hybridization has taken place (the so-called "detection step").

Several inspection methods and apparatuses are known for this purpose, for example of an optical or electrical type. In particular, the methods and apparatuses of an optical type are frequently based upon the phenomenon of fluorescence. The reactions of amplification and hybridization are carried out in such a way that the hybridized strands, contained in a detection chamber made in a substrate, include fluorescent molecules or fluorophores (the hybridized strands may be fixed to the bottom of the detection chamber or else remain in liquid suspension). The substrate is exposed to a light source having an appropriate spectrum of emission such as to excite the fluorophores. In turn, the excited fluorophores emit a secondary radiation at an emission wavelength greater than the peak of the excitation spectrum. The light emitted by the fluorophores is collected and detected by an optical sensor. In order to eliminate the background luminous radiation, representing a source of disturbance, the optical sensor is provided with band-pass filters centered at the emission wavelength of the fluorophores.

The detection of different substances in one and the same specimen requires as a rule the use of distinct fluorophores, having respective excitation and emission wavelengths. Various sets of optical filters must hence be coupled in succession to the light source and to the optical sensor for analyzing the responses in the excitation and emission bands of each fluorophore.

A limitation of known systems depends upon the need to envisage a mechanism of replacement of the filters, without which the analyses could not be conducted automatically. Mechanisms of this sort may comprise one or more carousels, mounted on which are the filters, and respective motors controlled to couple the pair of filters to the light source and to the optical sensor. This need, however, entails considerable overall dimensions, preventing production of independent portable analyzers.

Alternatively, it is possible to use multiple-band filters, but solutions of this type usually penalize the precision of detection. The excitation and emission bands of fluorophores of different types are in fact centered around different wavelengths, but have significant and partially overlapping tails. The optical multiple-band filters are in general less selective and are far from effective in preventing phenomena of mutual interference (referred to also as "crosstalk"). On account of the poor selectivity of multiple-band filters, in practice, the fluorophores can be excited also by stimuli of the excitation band of a different fluorophore and the optical sensor may collect light emitted by fluorophores different from those which are specifically excited (i.e., excited by tails of bands different from their own).

BRIEF SUMMARY

Some embodiments of the present provide an analyzer for biochemical analyses and a method for determining concentrations of fluorescent substances in a solution.

According to the present disclosure an analyzer for biochemical analyses and a method for determining concentrations of fluorescent substances in a solution are provided as defined in claim 1 and claim 10, respectively.

BRIEF DESCRIPTION OF THE SEVERAL VIEWS OF THE DRAWINGS

For a better understanding of the disclosure, some embodiments thereof will now be described, purely by way of non-limiting example and with reference to the attached drawings, wherein.

DETAILED DESCRIPTION

Figure 1:
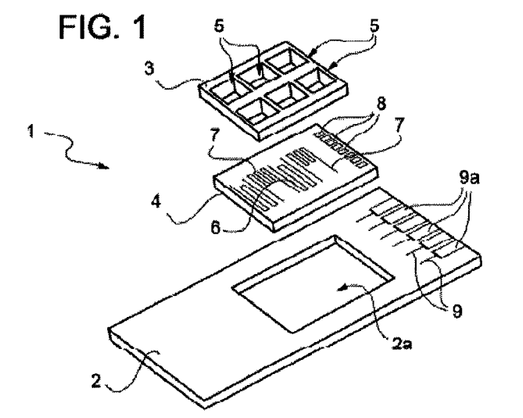
FIG. 1 is an exploded perspective view of a chemical microreactor.

The exploded view of FIG. 1 shows a microreactor 1 for biochemical analyses housed on an electronic printed-circuit board (PCB) 2. More precisely, the PCB 2 has a through opening 2a, where the microreactor 1 is housed.

For reasons of simplicity, in what follows reference will be made to microreactors and instrumentation for amplification of nucleic acids of polymerase chain reaction (PCR) and the analysis of the results of the amplification, without this possibly being considered as in any way limiting. What is described hereinafter, in fact, finds advantageous application also in systems designed for execution and detection of the results of different biochemical processes, in addition to amplification by means of PCR.

The microreactor 1 comprises a first chip 3, for example made of polymeric material, and a second chip 4, made of semiconductor material, joined to one another.

A plurality of wells 5 are made in the first chip 3 and are configured to receive solutions containing biological specimens to be analyzed. In one embodiment, the microreactor 1 has been functionalized by fixing DNA probes to the walls of the wells 5. The DNA probes can comprise individual DNA strands containing target sequences of nucleotides to be sought in the biological specimen analyzed.

Heaters 6 and on-board temperature sensors 7 are integrated in the second chip 4. The on-board temperature sensors 7 are of a thermoresistive type. In practice, their resistance varies as a function of temperature, and hence a reading of the resistance indicates the temperature at a given instant. The second chip 4 projects slightly on one side with respect to the first chip 3, and on the projecting part houses contact pads 8 for connection of the heaters 6 and of the on-board temperature sensors 7 to conductive paths 9 on the PCB 2. Terminals 9a of the paths 9 enable connection of the PCB 2 once it has been inserted in an analyzer.

For carrying out analyses of a specimen with the microreactor 1, a mixture of reagents in solution that comprises fluorophores of two types is introduced in the wells 5. A first type of fluorophores has an excitation wavelength $\lambda_{E1}$ and a detection wavelength (or emission wavelength) $\lambda_{D1}$ and is combined with a first substance to be sought. A second type of fluorophores has an excitation wavelength $\lambda_{E2}$ and a detection wavelength (or emission wavelength) $\lambda_{D2}$ and is combined with a second substance to be sought.

Figure 2:
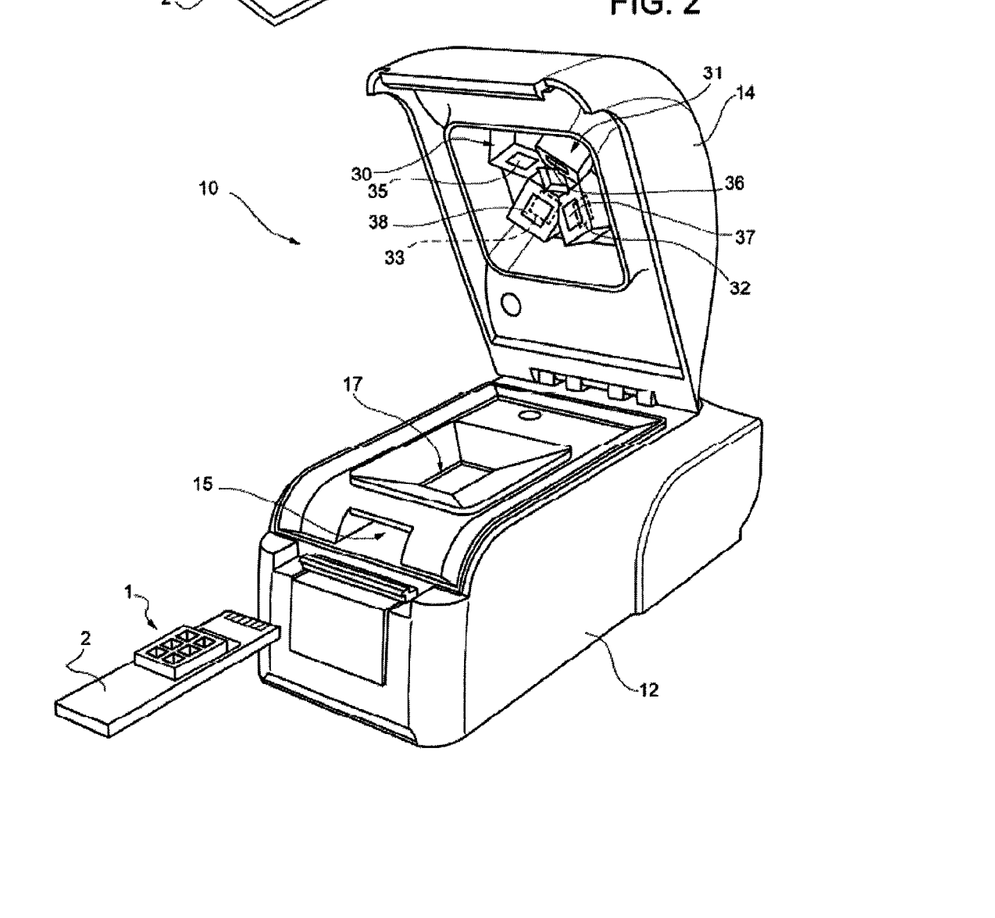
FIG. 2 is a perspective view of an analyzer for biochemical analyses according to one embodiment of the present disclosure.

As is shown in FIG. 2, a real-time PCR analyzer, designated as a whole by the reference number 10, comprises a first shell 12, closed at the bottom by a metal plate 13, and a second shell 14, hinged to the first shell 12. The first shell 12, the metal plate 13, and the second shell 14 define a casing of the analyzer 10.

Figure 3:
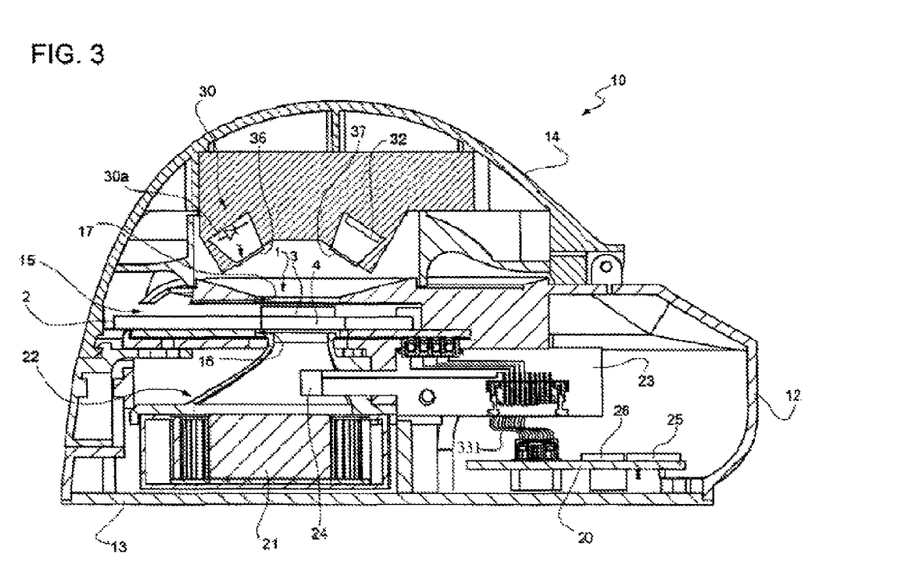
FIG. 3 is a side view, sectioned along a longitudinal plane, of the analyzer of FIG. 2.

With reference also to FIG. 3, the first shell 12 has a seat 15 for receiving the microreactor 1 mounted on the PCB 2. The seat 15 is accessible from outside for insertion of the PCB 2 with the microreactor 1 when the second shell 12 is open, in a raised position. In a position corresponding to the position of the microreactor 1 inserted in the seat 15, the first shell 12 has a first window 16 and a second window 17. The first window 16 sets the seat 15 in communication with the inside of the first shell 12, whereas the second window 17 enables observation of the microreactor 1 when the PCB 2 is inserted in the seat 15 and the second shell 14 is lifted.

Housed inside the first shell 12 (FIG. 3) are a control board 20, a fan 21, a collector 22, and a sensor board 23, mounted on which is a calibrated temperature sensor 24.

The control board 20 and the fan 21 are fixed to the metal plate 13.

The control board 20 is connected to sensor board 23 via wires 331 and houses a control unit 25, which presides over operation of the analyzer 1, as explained hereinafter, and at least one memory module 26.

In the embodiment described herein, the fan 21 is aligned to the windows 16, 17 and is operable to draw in air through the collector 22. More precisely, a flow of air is drawn in along a path that develops from the seat 15 to the fan 21 through the collector 22 in such a way as to cause a thermal exchange between the airflow and the microreactor 1 arranged in the seat 15.

The second shell 14 is hinged to the first shell 12 and defines a lid, shaped so as to be coupled in a light-proof way with the first shell 12 and obscure the second window 17. In practice, when the second shell 14 is closed on the first shell 12, the inside of the second shell 14 is substantially inaccessible to light, and the microreactor 1 inserted in the seat 15 is obscured.

When the second shell 14 is lifted, the seat 15 is accessible for inserting and removing the PCB 2 with the microreactor 1. When the PCB 2 is in the seat 15, moreover, the microreactor 1 is visible and accessible from outside for enabling operations of introduction of biological specimens to be analyzed.

Figure 4:
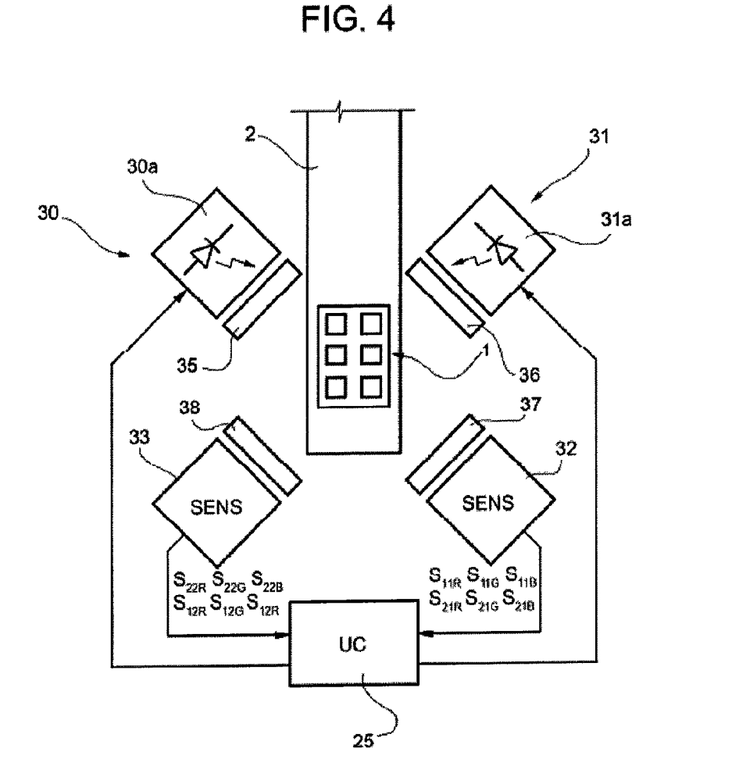
FIG. 4 is a top plan view of a detail of the analyzer of FIG. 2, with parts removed for reasons of clarity.

A first light source 30, a second light source 31, a first image sensor 32, and a second image sensor 33 are housed in the second shell 14 and are all controlled by the control unit 25, as shown also in FIG. 4.

Figure 5:
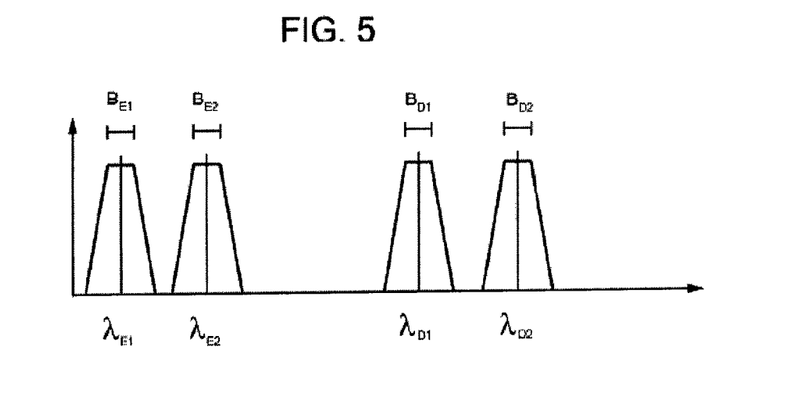
FIG. 5 is a graph that shows quantities regarding the analyzer of FIG. 2.

The first light source 30 and the second light source 31, comprising respective emitter devices 30a, 31a, for example of the LED type, are oriented so as to illuminate the microreactor 1 through the second window 17 and are provided, respectively, with a first excitation filter 35 and a second excitation filter 36 that intercept the radiation coming from the emitter device 30a and from the emitter device 31a, respectively. As shown in FIG. 5, the first excitation filter 35 and the second excitation filter 36 have respective excitation passbands $B_{E1}$, $B_{E2}$ centered around excitation wavelengths $\lambda_{E1}$, $\lambda_{E2}$ of fluorophores of two different types. The luminous radiation emitted by the first light source 30 and by the second light source 31 is hence substantially confined, respectively, in the excitation passband $B_{E1}$ of the first excitation filter 35 and in the excitation passband $B_{E2}$ and of the second excitation filter 36. The excitation passbands $B_{E1}$, $B_{E2}$ are moreover separate and non-overlapping.

The first image sensor 32 and the second image sensor 33 are arranged so as to receive the light emitted by the fluorophores present in the specimen contained in the microreactor 1 and excited by the light coming from the first light source 30 and from the second light source 31. In the embodiment described, the first light source 30 and the first image sensor 32 are aligned along a first axis X, parallel to the plane of the PCB 2 when the latter is located in the seat 15 and rotated through 45° with respect to a longitudinal axis of the PCB 2 in the seat 15. The second light source 31 and the second image sensor 33 are aligned along a second axis Y, perpendicular to the first axis X (FIG. 4).

The first image sensor 32 and the second image sensor 33 are provided, respectively, with a first detection filter 37 and a second detection filter 38. The first detection filter 37 and the second detection filter 38 have respective detection passbands $B_{D1}$, $B_{D2}$ centered around detection wavelengths (or emission wavelengths) $\lambda_{D1}$, $\lambda_{D2}$ of fluorophores of two different types (FIG. 5). The passbands $B_{D1}$, $B_{D2}$ of the first detection filter 37 and of the second detection filter 38 are moreover separate and non-overlapping and exclude, respectively, the passbands $B_{E1}$, $B_{E2}$ of the first excitation filter 35 and of the second excitation filter 36.

In the embodiment described, moreover, the first image sensor 32 and the second image sensor 33 are RGB sensors and supply each three respective signals for the red, green, and blue channels.

In fact, the RGB sensors comprise a plurality of photodetectors arranged in an array and provided each with a respective filter with a red, green, or blue color, with the green elements in a proportion twice than of the red and blue elements. A RGB sensor hence supplies three channel signals, one for each of the fundamental colors red, green, and blue, which are then combined with local-average operators for reconstructing the original colors of the detected image. Each image signal hence represents the same image filtered with a filter corresponding to one of the fundamental colors.

In particular, the first image sensor 32 supplies first channel signals, and the second image sensor 33 supplies second channel signals. More precisely, the first image sensor 32 supplies first channel signals $S_{11R}$, $S_{11G}$, $S_{11B}$, when the first light source 30 is activated, and first channel signals $S_{12R}$, $S_{12G}$, $S_{12B}$ when the second light source 31 is activated, and the second image sensor 33 supplies second channel signals $S_{21R}$, $S_{21G}$, $S_{21B}$, when the first light source 30 is activated and second channel signals $S_{22R}$, $S_{22G}$, $S_{22B}$ when the second light source 31 is activated. In what follows, the expression "image signals $S_I$" will be used to designate all the channel signals $S_{11R}$, $S_{11G}$, $S_{11B}$, $S_{12R}$, $S_{12G}$, $S_{12B}$, $S_{21R}$, $S_{21G}$, $S_{21B}$, $S_{22R}$, $S_{22G}$, $S_{22B}$ regarding one and the same image or portion of image (possibly also a single pixel).

The signals supplied by the first image sensor 32 and by the second image sensor 33 hence contain information regarding the response of each type of fluorophore in the bands of the fundamental colors, when either of the first light source 30 and the second light source 31 is activated.

The control unit 25 exploits the image signals $S_I$ to determine the presence and concentrations (possibly zero) in the specimen of substances being examined to which the fluorophores are bound. The control unit 25 uses the procedure described hereinafter with reference to FIG. 6.

Figure 6:
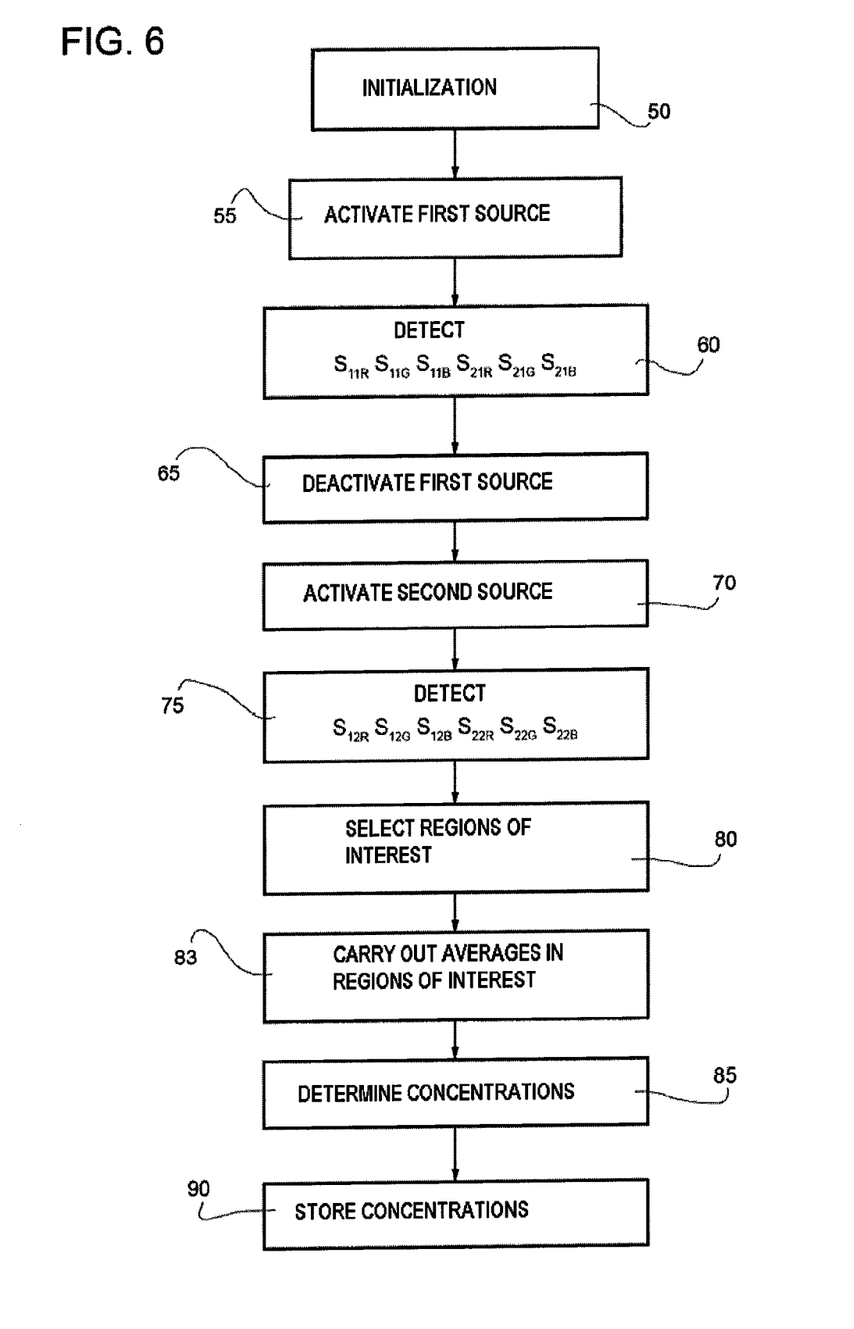
FIG. 6 is a flowchart regarding a method for determining concentrations of fluorescent substances in a solution according to one embodiment of the present disclosure.

After an initialization step (block 50), the control unit 25 activates the first light source 30 (block 55) and detects (block 60) both the first channel signals $S_{11R}$, $S_{11G}$, $S_{11B}$, associated to the fluorophores of the first type with detection wavelength $\lambda_{D1}$ (responding to the excitation wavelength $\lambda_{E1}$ of the first light source 30), and the second channel signals $S_{21R}$, $S_{21G}$, $S_{21B}$, associated to the fluorophores of the second type with detection wavelength $\lambda_{D2}$ (responding principally to the excitation wavelength $\lambda_{E2}$ of the second light source 31 and, secondarily, to tails of the excitation passband $B_{E1}$ of the first light source 30).

Next, the control unit 25 de-activates the first light source 30 (block 65), activates the second light source 31 (block 70) and detects (block 75) both the first channel signals $S_{12R}$, $S_{12G}$, $S_{12B}$, associated to the fluorophores of the first type with detection wavelength $\lambda_{D1}$ (responding to the excitation wavelength $\lambda_{E1}$ of the first light source 30 and, secondarily, to tails of the excitation passband $B_{E2}$ of the second light source 31), and the second channel signals $S_{22R}$, $S_{22G}$, $S_{22B}$, associated to the fluorophores of the second type with detection wavelength $\lambda_{D2}$ (responding principally to the excitation wavelength $\lambda_{E2}$ of the second light source 31).

The image signals $S_I$ thus obtained represent images defined by arrays of pixels.

Next (block 80), the control unit 25 selects in the images regions of interest, eliminating the portions of image which do not contain significant information. In the embodiment described, in particular, the selected regions of interest correspond to the wells 5 of the microreactor 1.

Then (block 83), the image signals $S_I$ detected are averaged over each region of interest, which is hence represented by a respective measurements vector $$S = [S^*_{11R} S^*_{11G} S^*_{11B} S^*_{12R} S^*_{12G} S^*_{12B} S^*_{21R} S^*_{21G} S^*_{21B} S^*_{22R} S^*_{22G} S^*_{22B}]'$$

(where the prime sign indicates the transposed; the measurements vector S is consequently a column vector). The symbol "*" indicates the respective mean value of each image signal $S_I$ in the region of interest.

The control unit 25 then processes the detected image signals $S_I$ to determine the concentrations $C_1$, $C_2$ of the fluorophores and hence of the substances sought in the specimen being examined (block 85).

For this purpose, it is noted that the following equation applies $$S = MC \tag{1}$$

where $C=[C_1 \; C_2]'$ is the column vector of the concentrations sought, and M is a crosstalk matrix defined as follows:

$$M = \begin{bmatrix} f_{111R} & f_{211R} \\ f_{111G} & f_{211G} \\ f_{111B} & f_{211B} \\ f_{112R} & f_{212R} \\ f_{112G} & f_{212G} \\ f_{112B} & f_{212B} \\ f_{121R} & f_{222R} \\ f_{121G} & f_{222G} \\ f_{121B} & f_{222B} \end{bmatrix}$$

In the first column of the crosstalk matrix M, the coefficients $f_{1JKR}$, $f_{1JKG}$, $f_{1JKB}$ represent the contributions, due to the first fluorophore, to the red, green, and blue channels (signals $S_{JKR}$, $S_{JKG}$, $S_{JKB}$) detected by the sensor J (J=1, 2, for the first image sensor 32 and the second image sensor 33, respectively) when the light source K is active (K=1, 2 for the first light source 30 and the second light source 31, respectively). Likewise, in the second column of the crosstalk matrix M, the coefficients $f_{2JKR}$, $f_{2JKG}$, $f_{2JKB}$, represent the contributions, due to the second fluorophore, to the red, green, and blue channels detected by the sensor J when the light source K is active.

The coefficients of the crosstalk matrix M can be determined experimentally, by carrying out measurements with standard calibration concentrations, or else in an analytical way by means of modeling or simulation, starting from the characteristic curves of the light sources, of the filters, of the image sensors, and of the fluorophores.

In order to determine the concentration vector C, the control unit 25 uses the pseudoinverse crosstalk matrix $M_{PI}$, i.e., the matrix that satisfies the equation $$M_{PI}M = I_{(2 \times 2)} \tag{2}$$

where $I_{(2 \times 2)}$ is the identity matrix with two rows and two columns.

The concentration vector C is determined by the control unit 25 as follows $$C = M_{PI}S \tag{3}$$

The concentrations thus determined (block 90) are stored in the memory module 26 and made available by the control unit 25 through an interface (not shown), for example a USB interface.

Figure 7:
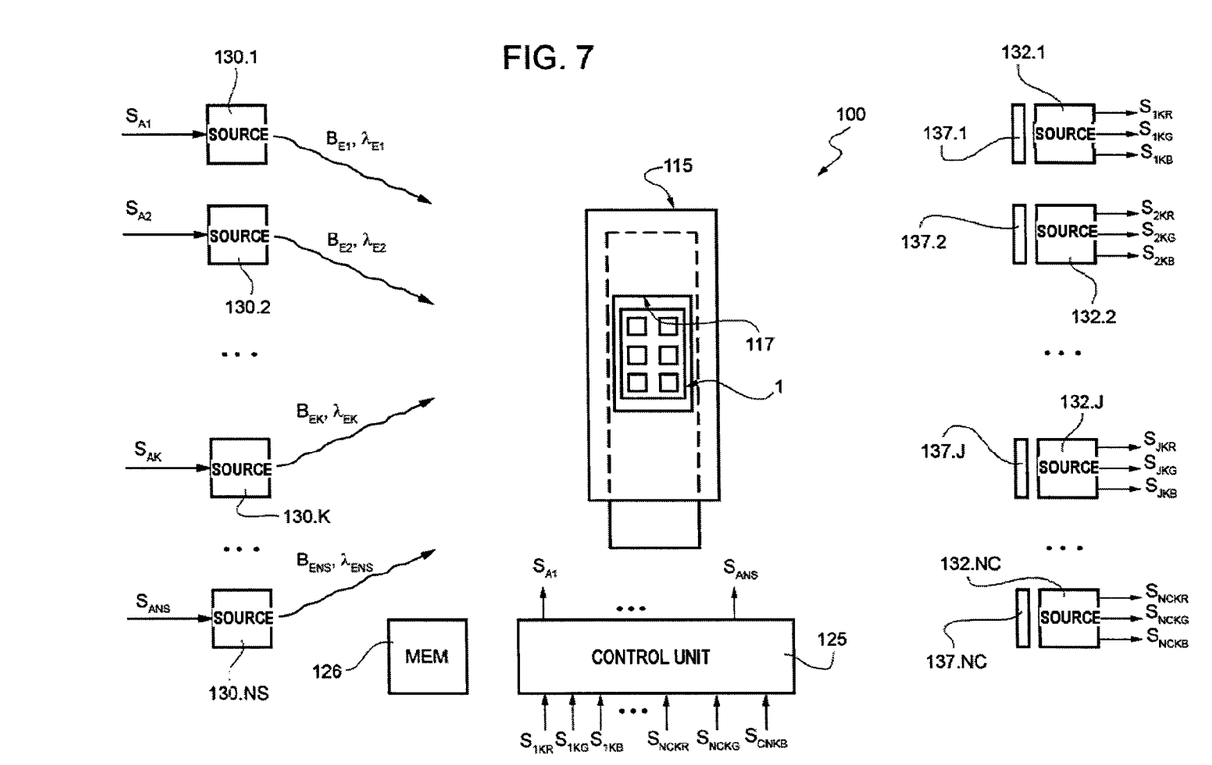
FIG. 7 is a simplified block diagram of an analyzer for biochemical analyses according to a different embodiment of the present disclosure.

FIG. 7 illustrates as a whole a different embodiment of the disclosure. In this case, an analyzer 100 is provided for detection of NF types of fluorophores having respective excitation wavelengths $\lambda_{E1}, \lambda_{E2}, \ldots, \lambda_{ENF}$ and respective detection wavelengths (or emission wavelengths) $\lambda_{D1}, \lambda_{D2}, \ldots, \lambda_{DNF}$ and combine with respective distinct substances to be sought.

The analyzer 100 comprises:

a seat 115, for receiving the microreactor 1, with a window 117 for rendering the microreactor 1 visible;

a control unit 125 with a memory module 126;

a number NS (greater than two) of light sources 130.1, 130.2, ..., 130.NS, each of which emits light in a respective excitation passband $B_{E1}, B_{E2}, \ldots, B_{ENS}$ and is oriented so as to illuminate the microreactor 1 through the window 117 when the microreactor 1 is introduced in the seat 115;

a number NC (greater than two) of RGB image sensors 132.1, 132.2, ..., 132.NC, each provided with a respective detection filter 137.1, 137.2, ..., 137.NC having a respective detection passband $B_{D1}, B_{D2}, \ldots, B_{DNS}$ and oriented so as to receive, through the window 117, light emitted by fluorophores contained in a specimen present in the microreactor 1 when they are excited by one of the light sources 130.1, 130.2, ..., 130.NS.

The generic image sensor 132.J supplies to the control unit 125 respective channel signals $S_{JKR}$, $S_{JKG}$, $S_{JKB}$ when the microreactor 1 is illuminated by the light source 130.K.

The control unit 125 exploits the image signals $S_I$ to determine the presence and concentrations (possibly zero) in the specimen of substances being examined, to which the fluorophores are bound. The control unit 125 uses the procedure described hereinafter with reference to FIG. 8.

Figure 8:
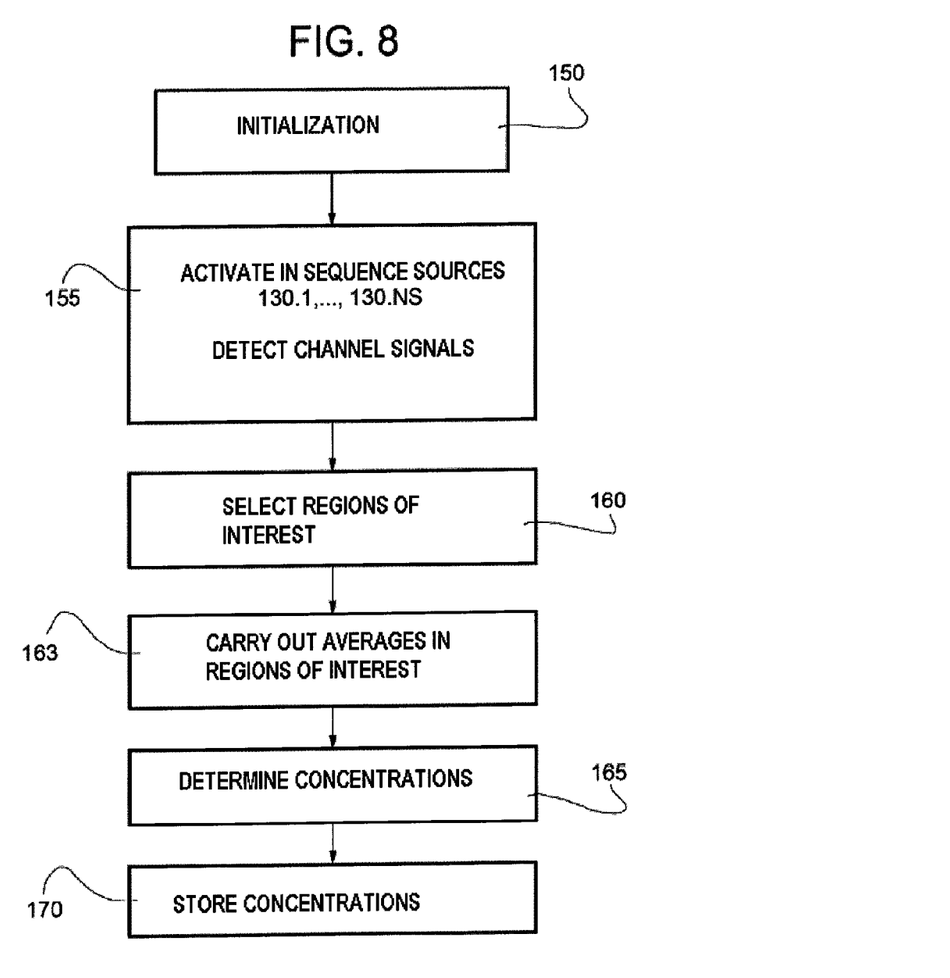
FIG. 8 is a flowchart regarding a method for determining concentrations of fluorescent substances in a solution according to a different embodiment of the present disclosure.

After an initialization step (block 150), the control unit 125 activates in sequence selectively one of the light sources 130.1, 130.2, ..., 130.NS once by respective activation signals $S_{A1}$, $S_{A2}$, ..., $S_{ANS}$ and detects the corresponding 3*NS*NC channel signals supplied by the image sensors 132.1, 132.2, ..., 132.NC (block 155). For example, when the generic light source 130.K is activated, the generic image sensor 132.J supplies the signals $S_{JKR}$, $S_{JKG}$, $S_{JKB}$.

When all the light sources 130.1, 130.2, ..., 130.NS have been activated and the corresponding channel signals detected, the control unit 125 then selects regions of interest, eliminating the portions of image without significant information (block 160).

Then (block 163), the image signals $S_I$ detected are averaged over each region of interest, which is hence represented by a respective a measurements vector $$S = [S^*_{11R} S^*_{11G} S^*_{11B} \ldots S^*_{NSR} S^*_{NSG} S^*_{NSB} S^*_{21R} S^*_{21G} S^*_{21B} \ldots S^*_{NCNSR} S^*_{NCNSG} S^*_{NCNSB}]'$$

The symbol "*" indicates the respective mean value of each image signal $S_I$ in the region of interest.

The control unit 125 then processes the image signals $S_I$ detected to determine the concentrations $C_1, C_2, \ldots, C_{NF}$ of the fluorophores and hence of the substances sought in the specimen being examined (block 165).

For this purpose, it has been noted that the following equation applies:

$$Sg = MgCg \quad (4)$$

where $Cg = [C_1\ C_2\ \ldots\ C_{NF}]'$ is the column vector of the concentrations sought, and Mg is a crosstalk matrix defined as follows $$Mg = \begin{bmatrix} f_{111R} & f_{211R} & \cdots & f_{NF11R} \\ f_{111G} & f_{211G} & \cdots & f_{NF11G} \\ f_{111B} & f_{211B} & \cdots & f_{NF11B} \\ \cdots & \cdots & \cdots & \cdots \\ f_{11NSR} & f_{21NSR} & \cdots & f_{NF1NSR} \\ f_{11NSG} & f_{21NSG} & \cdots & f_{NF1NSG} \\ f_{11NSB} & f_{21NSB} & \cdots & f_{NF1NSB} \\ f_{121R} & f_{221R} & \cdots & f_{NF21R} \\ f_{121G} & f_{221G} & \cdots & f_{NF21G} \\ f_{121B} & f_{221B} & \cdots & f_{NF21B} \\ \cdots & \cdots & \cdots & \cdots \\ f_{1NCNSR} & f_{2NCNSR} & \cdots & f_{NFNCNSR} \\ f_{1NCNSG} & f_{2NCNSG} & \cdots & f_{NFNCNSG} \\ f_{1NCNSB} & f_{2NCNSB} & \cdots & f_{NFNCNSB} \end{bmatrix}$$

The generic coefficients $f_{IJKR}$, $f_{IJKG}$, $f_{IJKB}$ of the crosstalk matrix Mg represent the contributions, due to the fluorophore I ($I=1, 2, \ldots, NF$), to the red, green, and blue channels (signals $S_{JKR}$, $S_{JKG}$, $S_{JKB}$) detected by the sensor J ($J=1, 2, \ldots, NC$) when the light source K ($K=1, 2, \ldots, NS$) is active.

To determine the concentration vector Cg, the control unit 125 uses the pseudoinverse crosstalk matrix $Mg_{PI}$, i.e., the matrix that satisfies the equation:

$$Mg_{PI} Mg = I_{(NF \times NF)} \quad (5)$$

where $I_{(NF \times NF)}$ is the identity matrix having NF rows and NF columns.

The concentration vector Cg is determined by the control unit 125 as follows $$Cg = Mg_{PI} Sg \quad (6)$$

The concentrations thus determined (block 170) are stored in the memory module 126 and made available by the control unit 125 through an interface (not shown), for example a USB interface.

Thanks to the methods and devices described, in the first place the analysis of the specimens, in particular the determination of the concentrations of substances sought, can be carried out in an accurate way and, at the same time, without any need for mechanisms for replacement of the excitation filters coupled to the light sources. The precision is greater as compared to devices that use multiple-band filters, which are normally less selective, especially when the separation between the emission bands of the fluorophores is not large. In addition, given that different light sources are present, each with its own single-band filter, no replacement of the filters is required. It is hence possible to produce mechanically simpler devices, which are less subject to failure and more compact. In turn, the contained dimensions favor the design and manufacture of portable analyzers, which can be conveniently used not only in the laboratory, but also in field.

In addition, the use of image sensors of an RGB type allows to exploit the separation in channels. The RGB image sensors carry out internally filtering by decomposition of the light into the channels corresponding to the primary colors red, green, and blue. This contributes further to reducing interference between sensors in the presence of crosstalk phenomena. In practice, the contributions of the various channels, each of which carries a specific information content, are weighted and combined by the crosstalk matrices. In this way, it is possible to determine with greater precision the concentrations of the substances sought.

Figure 9:
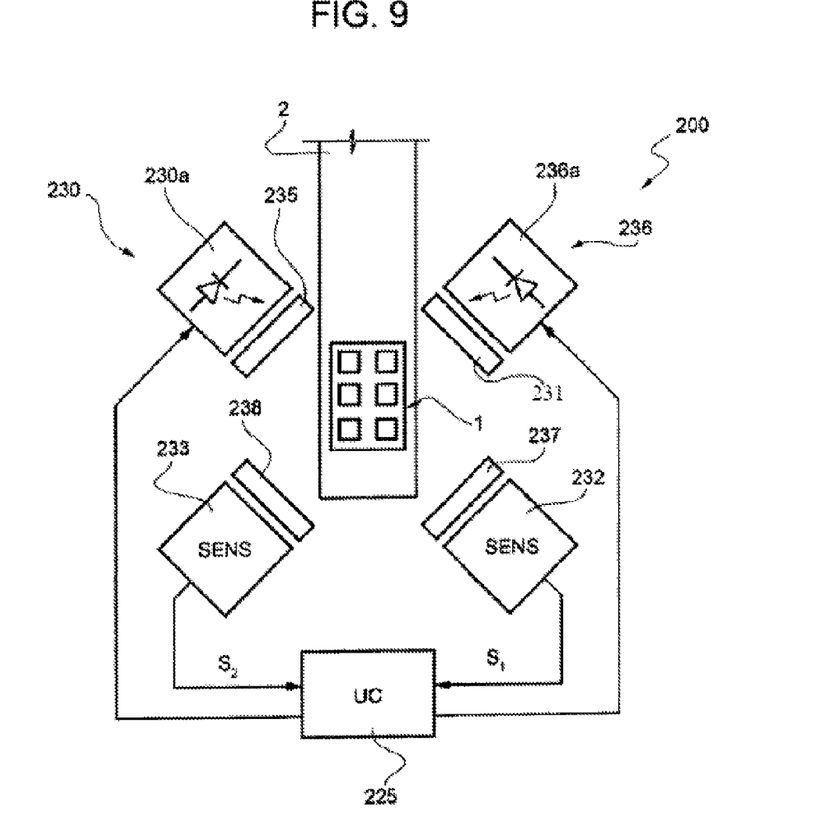
FIG. 9 is a top plan view of a detail of the analyzer of FIG. 7 with parts removed for reasons of clarity.

In a further embodiment, illustrated as a whole in FIG. 9, an analyzer 200 has substantially the same structure already described with reference to FIGS. 2-5 and, in particular, comprises a first light source 230 including light 230a with a first excitation filter 235, a second light source 236 including light 236a with a second excitation filter 231, a first image sensor 232 with a first detection filter 237, a second image sensor 233 with a second detection filter 238, a control unit 225, and a memory module 226. In this case, the first image sensor 232 and the second image sensor 233 are of a single-channel monochromatic type and supply, respectively, a first detection signal S1 and a second detection signal S2 to the control unit 225, which processes them to obtain concentrations C1, C2 of fluorophores.

The control unit 225 activates in sequence the first light source 230 and the second light source 231 and detects the first detection signal $S_1$ and the second detection signal $S_2$. In addition, the control unit 225 uses the inverse of the crosstalk matrix Mc given by $$Mc = \begin{bmatrix} f_{11} & f_{12} \\ f_{21} & f_{22} \end{bmatrix}$$

to determine the concentration vector C=[$C_1$ $C_2$]'. More precisely, the concentration vector C=[$C_1$ $C_2$]' is determined on the basis of the equation:

$$C = Mc^{-1}Sc$$

where $Mc^{-1}$ is the inverse matrix of the crosstalk matrix Mc.

Modifications and variations may be made to the device and to the method described, without thereby departing from the scope of the present disclosure.

The various embodiments described above can be combined to provide further embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. An analyzer for biochemical analysis comprising:
   i) a seat configured to accommodate a recipient;
   ii) a first light source configured to provide luminous radiation in a first excitation band, including a first excitation wavelength of fluorophores of a first type, and oriented so as to illuminate the recipient when the recipient is accommodated by the seat;
   iii) a first image sensor arranged to receive light emitted by fluorophores contained in the recipient when the recipient is accommodated by the seat, the first image sensor including a first detection filter, having a first detection passband that includes a first emission wavelength of the fluorophores of the first type;
   iv) a second light source configured to provide luminous radiation in a second excitation band, including a second excitation wavelength of fluorophores of a second type, and oriented so as to illuminate the recipient when the recipient is accommodated by the seat;
   v) a second image sensor arranged so as to receive light emitted by fluorophores contained in the recipient when the recipient is accommodated by the seat, the second image sensor including a second detection filter having a second detection passband that includes a second emission wavelength of the fluorophores of the second type;
   vi) a control unit coupled to the first light source, the second light source, the first image sensor, and the second image sensor, and configured to activate, in succession, selectively one of the first light source and the second light source, and receive image signals from the first image sensor and the second image sensor;
   vii) wherein the first image sensor includes a red channel, a green channel, and a blue channel configured to receive first channel signals of the image signals;
   the second image sensor includes a red channel, to a green channel and to a blue channel configured to receive second channel signals of the image signals;
   viii) wherein the control unit is configured to weigh and combine the first channel signals and the second channel signals for determining concentrations of substances contained in the recipient.

2. An analyzer for biochemical analysis comprising:
   i) a seat configured to accommodate a recipient;
   ii) a first light source configured to provide luminous radiation in a first excitation band, including a first excitation wavelength of fluorophores of a first type, and oriented so as to illuminate the recipient when the recipient is accommodated by the seat;
   iii) a first image sensor having red, blue and green channels and arranged to receive light emitted by fluorophores contained in the recipient when the recipient is accommodated by the seat, the first image sensor including a first detection filter, having a first detection passband that includes a first emission wavelength of the fluorophores of the first type;
   iv) a second light source configured to provide luminous radiation in a second excitation band, including a second excitation wavelength of fluorophores of a second type, and oriented so as to illuminate the recipient when the recipient is accommodated by the seat;
   v) a second image sensor having red, blue and green channels and arranged so as to receive light emitted by fluorophores contained in the recipient when the recipient is accommodated by the seat, the second image sensor including a second detection filter having a second detection passband that includes a second emission wavelength of the fluorophores of the second type;
   vi) a control unit coupled to the first light source, the second light source, the first image sensor, and the second image sensor, and configured to activate, in succession, selectively one of the first light source and the second light source, and receive image signals from the first image sensor and the second image sensor; and
   ix) wherein the control unit is configured to determine concentrations of substances contained in the recipient according to the equation $C = M_{PI} S$
   where C is a concentrations vector that indicates concentrations of a first substance, capable of binding to fluorophores of the first type, and of a second substance, capable of binding to fluorophores of the second type, S is a measurements vector indicative of values of the first channel signals and of the second channel signals and $M_{PI}$ is a pseudo-inverse matrix of a coefficient matrix M defined as $$M = \begin{bmatrix} f_{111R} & f_{211R} \\ f_{111G} & f_{211G} \\ f_{111B} & f_{211B} \\ f_{112R} & f_{212R} \\ f_{112G} & f_{212G} \\ f_{112B} & f_{212B} \\ f_{121R} & f_{221R} \\ f_{121G} & f_{221G} \\ f_{121B} & f_{221B} \\ f_{122R} & f_{222R} \\ f_{122G} & f_{222G} \\ f_{122B} & f_{222B} \end{bmatrix}$$

where coefficients $f_{1JKR}$, $f_{1JKG}$, $f_{1JKB}$, J=1, 2 and K=1, 2, are representative of contributions to respectively the red, green and blue channels, caused by fluorophores of the first type, which the first image sensor is configured to detect, and coefficients $f_{2JKR}$, $f_{2JKG}$, $f_{2JKB}$, J=1, 2 and K=1, 2, are representative of contributions to respectively the red, green and blue channels, caused by fluorophores of the second type, which the second image sensor is configured to detect.

3. An analyzer for biochemical analysis comprising:
   i) a seat configured to accommodate a recipient;
   ii) a first light source configured to provide luminous radiation in a first excitation band, including a first excitation wavelength of fluorophores of a first type, and oriented so as to illuminate the recipient when the recipient is accommodated by the seat;
   iii) a first image sensor having red, blue and green channels and arranged to receive light emitted by fluorophores contained in the recipient when the recipient is accommodated by the seat, the first image sensor including a first detection filter, having a first detection passband that includes a first emission wavelength of the fluorophores of the first type;

iv) a second light source configured to provide luminous radiation in a second excitation band, including a second excitation wavelength of fluorophores of a second type, and oriented so as to illuminate the recipient when the recipient is accommodated by the seat;

v) a second image sensor having red, blue and green channels and arranged so as to receive light emitted by fluorophores contained in the recipient when the recipient is accommodated by the seat, the second image sensor including a second detection filter having a second detection passband that includes a second emission wavelength of the fluorophores of the second type;

vi) a control unit coupled to the first light source, the second light source, the first image sensor, and the second image sensor, and configured to activate, in succession, selectively one of the first light source and the second light source, and receive image signals from the first image sensor and the second image sensor; and ix) a number NC of image sensors greater than two, the number NC of image sensors including the first and second image sensors; and x) a number NS of light sources greater than two, the number NS of light sources including the first and second light sources, wherein:

the control unit is configured to activate, in succession, selectively one of the light sources and to determine the concentrations according to the equation:

$$Cg = Mg_{PI} Sg$$

where Cg is a concentrations vector indicative of concentrations of a plurality of substances, capable of binding each to fluorophores of a respective type among a number NF of types of analyzable fluorophores, Sg is a measurements vector containing values of channel signals provided by the image sensors and $Mg_{PI}$ is a pseudo-inverse matrix of a coefficient matrix Mg defined as:

$$Mg = \begin{bmatrix} f_{111R} & f_{211R} & \cdots & f_{NF11R} \\ f_{111G} & f_{211G} & \cdots & f_{NF11G} \\ f_{111B} & f_{211B} & \cdots & f_{NF11B} \\ \cdots & \cdots & \cdots & \cdots \\ f_{11NSR} & f_{21NSR} & \cdots & f_{NF1NSR} \\ f_{11NSG} & f_{21NSG} & \cdots & f_{NF1NSG} \\ f_{11NSB} & f_{21NSB} & \cdots & f_{NF1NSB} \\ f_{121R} & f_{221R} & \cdots & f_{NF21R} \\ f_{121G} & f_{221G} & \cdots & f_{NF21G} \\ f_{121B} & f_{221B} & \cdots & f_{NF21B} \\ \cdots & \cdots & \cdots & \cdots \\ f_{1NCNSR} & f_{2NCNSR} & \cdots & f_{NFNCNSR} \\ f_{1NCNSG} & f_{2NCNSG} & \cdots & f_{NFNCNSG} \\ f_{1NCNSB} & f_{2NCNSB} & \cdots & f_{NFNCNSB} \end{bmatrix}$$

wherein coefficients $f_{IJKR}$, $f_{IJKG}$, $f_{IJKB}$ are representative of contributions, caused by fluorophores of I-th type, with J=1, 2, ..., NF, to respectively the red, green and blue channels of the J-th image sensor, with J=1, 2, ..., NC, when the K-th light source, with K=1, 2, ..., NS is active.

4. An analyzer according to claim 3, wherein each light source, is configured to provide luminous radiation in a respective excitation band, that includes an excitation wavelength of fluorophores of a respective type, and is oriented so as to illuminate the recipient when the recipient is accommodated by the seat.

5. An analyzer according to claim 3, wherein each image sensor is arranged so as to receive light emitted by fluorophores contained in the recipient when the recipient is accommodated by the seat and includes a respective detection filter having a detection passband that includes an emission wavelength of fluorophores of a respective type.

6. A method of determining concentrations of fluorescent substances in a solution, comprising:

i) illuminating a recipient, containing a solution, by first light source configured to provide luminous radiation in a first excitation band, including a first excitation wavelength of fluorophores of a first type;

ii) detecting images of the recipient through a first image sensor having red, blue and green channels and that includes a first detection filter having a first detection passband that includes a first emission wavelength of the fluorophores of the first type;

iii) successively illuminating the recipient by a second light source configured to provide luminous radiation in a second excitation band, including a second excitation wavelength of fluorophores of a second type; and iv) detecting images of the recipient through a second image sensor having red, blue and green channels and that includes a second detection filter having a second detection passband that includes a second emission wavelength of the fluorophores of the second type;

v) determining concentrations of substances contained in the recipient based on the first channel signals and the second channel signals by weighing and combining the first channel signals and the second channel signals.

7. A method of determining concentrations of fluorescent substances in a solution, comprising:

i) illuminating a recipient, containing a solution, by first light source configured to provide luminous radiation in a first excitation band, including a first excitation wavelength of fluorophores of a first type;

ii) detecting images of the recipient through a first image sensor having red, blue and green channels and that includes a first detection filter having a first detection passband that includes a first emission wavelength of the fluorophores of the first type;

iii) successively illuminating the recipient by a second light source configured to provide luminous radiation in a second excitation band, including a second excitation wavelength of fluorophores of a second type; and iv) detecting images of the recipient through a second image sensor having red blue and green channels and that includes a second detection filter having a second detection passband that includes a second emission wavelength of the fluorophores of the second type;

v) determining concentrations of substances contained in the recipient based on the first channel signals and the second channel signals by weighing and combining the first channel signals and the second channel signals;

vi) wherein determining concentrations comprises using the equation:

$$C = M_{PI} S$$

where C is a concentrations vector indicative of concentrations of a first substance, capable of binding to fluorophores of the first type, and of a second substance, capable of binding to fluorophores of the second type, S is a measurements vector indicative of values of the first channel signals and of the second channel signals and $M_{PI}$ is a pseudo-inverse matrix of a coefficient matrix M defined as $$M = \begin{bmatrix} f_{111R} & f_{211R} \\ f_{111G} & f_{211G} \\ f_{111B} & f_{211B} \\ f_{112R} & f_{212R} \\ f_{112G} & f_{212G} \\ f_{112B} & f_{212B} \\ f_{121R} & f_{221R} \\ f_{121G} & f_{221G} \\ f_{121B} & f_{221B} \\ f_{122R} & f_{222R} \\ f_{122G} & f_{222G} \\ f_{122B} & f_{222B} \end{bmatrix}$$

where coefficients $f_{1JKR}$, $f_{1JKG}$, $f_{1JKB}$, J=1, 2 and K=1, 2, are representative of contributions to respectively the red, green and blue channels, caused by fluorophores of the first type, detected by the first image sensor and coefficients $f_{2JKR}$, $f_{2JKG}$, $f_{2JKB}$, J=1, 2 and K=1, 2, are representative of contributions to respectively the red, green and blue channels, caused by fluorophores of the second type, detected by the second image sensor.

\* \* \* \* \*